United States Patent
Krueger et al.

(10) Patent No.: US 11,972,857 B2
(45) Date of Patent: Apr. 30, 2024

(54) AUTOMATED SUBJECT MONITORING FOR MEDICAL IMAGING

(71) Applicant: KONINKLIJKE PHILIPS N.V., Eindhoven (NL)

(72) Inventors: Sascha Krueger, Hamburg (DE); Julien Senegas, Hamburg (DE); Peter Koken, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 779 days.

(21) Appl. No.: 17/049,605

(22) PCT Filed: Apr. 18, 2019

(86) PCT No.: PCT/EP2019/060157
§ 371 (c)(1),
(2) Date: Oct. 22, 2020

(87) PCT Pub. No.: WO2019/206819
PCT Pub. Date: Oct. 31, 2019

(65) Prior Publication Data
US 2021/0280297 A1    Sep. 9, 2021

(30) Foreign Application Priority Data

Apr. 23, 2018    (EP) .................................... 18168714

(51) Int. Cl.
*G16H 30/20*        (2018.01)
*G06T 7/00*         (2017.01)
(Continued)

(52) U.S. Cl.
CPC ........... *G16H 30/20* (2018.01); *G06T 7/0014* (2013.01); *G06T 7/75* (2017.01); *G16H 30/40* (2018.01)

(58) Field of Classification Search
CPC . G06T 2207/10081; G06T 2207/10088; G06T 2207/30196; G06T 7/0014;
(Continued)

(56) References Cited

U.S. PATENT DOCUMENTS

2008/0247599 A1    10/2008    Porikli
2011/0135190 A1    6/2011    Maad
(Continued)

FOREIGN PATENT DOCUMENTS

CN    105827946 A    8/2016
WO    2008004222 A1    1/2008

OTHER PUBLICATIONS

Search Report and Written Opinion from PCT/EP2019/060157 dated Jul. 18, 2019.

*Primary Examiner* — Mark D Remaly

(57) ABSTRACT

The invention provides for a medical instrument (100, 600) that comprises a medical imaging system (102, 102'), a subject support (110), and a camera system (104) configured for imaging the subject support in an initial position. The execution the machine executable instructions causes a processor (108) to: place (500) the subject support in the initial position (116); control (502) the camera system to acquire a series of repeated images (142); detect (506) the placement of one or more background objects (200); detect (508) one or more foreground objects (704); construct (510) a background object surface image (202) at least partially by stitching together the series of repeated images to replace image regions containing background objects obscured by the one or more foreground objects; determine (512) a three-dimensional object surface (208) using the background object surface image; detect (514) the subject in one of the series of repeated images (312); calculate (516) a subject segmentation (304) of the subject in the one of the series of repeated images; determine (518) a visible subject (Continued)

surface (308) using the subject segmentation and the one of the series of repeated images; and calculate (520) a three-dimensional subject model (310) by estimating a volume (314) defined by the three-dimensional object surface and the visible subject surface.

15 Claims, 7 Drawing Sheets

(51) Int. Cl.
*G06T 7/73* (2017.01)
*G16H 30/40* (2018.01)

(58) Field of Classification Search
CPC .. G06T 7/215; G06T 7/73; G06T 7/75; G16H 30/20; G16H 30/40
See application file for complete search history.

(56) References Cited

U.S. PATENT DOCUMENTS

| | | |
|---|---|---|
| 2015/0035942 A1 | 2/2015 | Hampton et al. |
| 2015/0348311 A1 | 12/2015 | Saur et al. |
| 2016/0050368 A1 | 2/2016 | Seo et al. |

AUTOMATED SUBJECT MONITORING FOR MEDICAL IMAGING

CROSS REFERENCE TO RELATED APPLICATIONS

This application is a U.S. national phase application of International Application No. PCT/EP2019/060157 filed Apr. 18, 2019, which claims the benefit of EP Application Ser. No. 18168714.6 filed Apr. 23, 2018 and is incorporated herein by reference.

FIELD OF THE INVENTION

The invention relates to medical imaging, in particular to magnetic resonance imaging or computed tomography.

BACKGROUND OF THE INVENTION

In medical imaging systems that use imaging modalities such as magnetic resonance imaging (MRI) or computed tomography (CT), the proper arrangement of a subject being imaged as well as other objects such as cushions, antennas, or other objects can be time consuming.

U.S. patent application publication US 2016/0050368 A1. Discloses a video processing apparatus. The video processing apparatus includes: a storage configured to store a video captured by a camera; and a controller configured to separate a target object from a background image in each of a plurality of key frames contained in the video, stitch separated background images to generate a panoramic background image, synthesize the target object with the panoramic background image to acquire a plurality of panoramic images corresponding to the plurality of key frames, and combine the panoramic images in a time axis to generate a panoramic video.

SUMMARY OF THE INVENTION

The invention provides for a medical instrument, a computer program product, and a method in the independent claims. Embodiments are given in the dependent claims.

Embodiments may provide for a means of providing detailed information about the position of a subject in the form of a three-dimensional subject model to aid in preparation to image the subject in a medical imaging system. When preparing to perform a medical imaging protocol using a medical imaging system various background objects may be placed on a support surface of a subject support before the subject is positioned. A camera system can be used to either measure directly or infer the location of surfaces defined by the subject support and the background objects placed on the subject support. These surfaces can be represented as the three-dimensional subject support model and the three-dimensional object surface respectively. When a subject is placed on the subject support, the camera system can be used to image the subject and measure directly or infer a subject model that represents the three-dimensional volume of the subject. The three-dimensional subject support model and the three-dimensional object surface can be used define the back of the subject which is away from the camera system. When placing background objects on the subject support, a foreground objects (such as an operator of the medical instrument) may obscure the view of the background objects. By stitching together images from a series of repeated images, such as a video feed, a more complete view of the background objects can be constructed.

In one aspect the invention provides for a medical instrument comprising a medical imaging system for acquiring medical imaging data from a subject within an imaging zone. The medical instrument further comprises a subject support with a support surface. The support surface is configured for receiving the subject. The subject support is configured for supporting the subject in an initial position wherein in the initial position the subject is outside of the imaging zone.

The medical instrument further comprises a camera system configured for imaging the support surface when the subject support is in the initial position. The medical instrument further comprises a memory containing or comprising machine-executable instructions. The medical instrument further comprises a processor for controlling the medical instrument. Execution of the machine-executable instructions causes the processor to place the subject support in the initial position. Execution of the machine-executable instructions further causes the processor to control the camera system to repeatedly acquire a series of repeated images.

Execution of the machine-executable instructions further cause the processor to detect the placement of one or more background objects that at least partially obscure the subject support surface within or using the series of repeated images. Execution of the machine-executable instructions further cause the processor to detect one or more foreground objects that obscure at least a portion of the one or more background objects in the series of repeated images. Execution of the machine-executable instructions further cause the processor to construct a background object surface image at least partially by stitching together the series of repeated images to replace image regions containing background objects obscured by the one or more foreground objects. Execution of the machine-executable instructions further cause the processor to determine a three-dimensional object surface using the background object surface image. Execution of the machine-executable instructions further cause the processor to detect the subject in one of the series of repeated images.

Execution of the machine-executable instructions further cause the processor to calculate a subject segmentation of the subject in the one of the series of repeated images. Execution of the machine-executable instructions further cause the processor to determine a visible subject surface using the subject segmentation and the one of the series of repeated images. Execution of the machine-executable instructions further cause the processor to calculate a three-dimensional subject model by estimating a volume defined by the three-dimensional object surface and the visible subject surface. This embodiment may be beneficial because it may provide for a means of estimating the volume of the subject and the position of the subject.

The invention concerns to acquire (repeatedly) successive images which show one or more background object being placed or (re)moved from the subject support (patient table). Further, (a part) of the successive images show foreground objects (e.g. the subject to be imaged). The background object may obscure (from the point of view of the camera) the support surface and the foreground object may obscure the background objects. The foreground objects may be eliminated by stitching images e.g. by replacing the image in which a background was obscured by another images in which the obstructing foreground object was not present or at a different location. This allows to generated the 3D-object surface of the scene with (only) the background objects in position. The subjects me be headrests, knee supports and other forms of cushions on the patient table on which the patient to be examined is positioned.

Further the subject is detected from the point of view of the camera while obstructing the view onto the background objects on the subject support. From the detection of the subject a visible (from the camera point of view) a subject segmentation is segmented form the collection of images of eh subject, background and subject support. This provides a surface rendering of the subject in as far as directly visible from the camera point of view. Finally from the visible subject surface and the 3D-object surface a volumetric representation of the subject is derived in the form of a calculated 3D subject model. An insight of the present invention is that the 3D-object surface corresponds with the rear surface of the subject that is away from the view of the camera because obstructed by the subject itself. Further, from the calculated 3D subject model any parts of the background objects may be eliminated that may still be visible form the camera point of view with the subject placed on the subject support. Accordingly an accurate segmentation of the subject from the background objects and the subject support is achieved that accurately represents the volume of the subject.

In some examples the camera system could be a camera system that takes a series of repeated still images. In other examples the camera system could be a video system that provides a continuous video feed.

In various examples the recognition of objects in the images such as the subject or the background, or foreground objects could be detected in different ways. For example, this could be done using a deformable model, a landmark detection or even an artificial intelligence module. For example, a convolution neural network may be trained to readily identify particular objects within an image.

The various specific foreground objects can be recognized and excluded from the background. Such objects may include magnetic resonance coils, magnetic resonance antennas, people, subjects, electrodes, hearing protectors, or other medical instruments.

The repeatedly acquired images may take different forms in different examples. This may in some examples mean images that are acquired sequentially or successively, it may mean images that are acquired continually or on a repeated, i.e. one discrete frame of the other basis, or it may even mean a video feed.

In another embodiment, execution of the machine-executable instructions further causes the processor to receive a registration of a three-dimensional subject support model to the series of repeated images. In some examples the relationship of the three-dimensional subject support to the images may be known a priori. In other examples the registration may be determined from the series of images itself. The three-dimensional subject support model is descriptive of a three-dimensional structure of the support surface. The three-dimensional subject support model can be used to at least partially construct the three-dimensional object surface.

In another embodiment, in a second position the subject support is configured for supporting at least a portion of the subject within the imaging zone.

In another embodiment the subject support is configured for transporting the subject from an initial position to the second position. Execution of the machine-executable instructions further cause the processor to move the subject support from the initial position to the second position. The second position is determined at least partially using the three-dimensional subject model. For example, the three-dimensional subject model may be used to roughly determine the position of the subject with respect to a model or anatomical landmark that are fit or registered to the three-dimensional subject model. This embodiment may be beneficial because it may eliminate the need for a light visor or other means for identifying the position of the subject before moving the subject into the imaging zone.

In another embodiment execution of the machine-executable instructions further cause the processor to control the medical imaging system to acquire the medical imaging data.

In another embodiment the medical imaging system is a magnetic resonance imaging system. The memory further contains pulse sequence commands configured for controlling the magnetic resonance imaging system to acquire the medical imaging data from a region of interest in the imaging zone. This embodiment may be beneficial because the use of the three-dimensional subject model may provide benefits in moving the subject into the right position or even for adjusting various parameters during the magnetic resonance imaging scan.

In another embodiment execution of the machine-executable instructions further cause the processor to fit a region of interest to the three-dimensional subject model. Execution of the machine-executable instructions further cause the processor to modify the pulse sequence commands to image the fitted region of interest. This embodiment may be beneficial because it may eliminate the need for a survey scan or may allow to acquire a survey scan with smaller FOV or higher resolution or with shorter duration or with a combination thereof. A survey scan is typically a lower resolution image that is acquired before data which is used to make clinical images is performed. The modification of the pulse sequence commands may include modifying various parameters or characteristics of the pulse sequence or magnetic resonance imaging protocol that is followed.

In another embodiment execution of the machine-executable instructions further causes the processor to identify at least a portion of the one or more foreground objects that are stationary in at least a predetermined number of sequential frames in the series of repeated images. Execution of the machine-executable instructions further cause the processor to determine if at least a portion of the one or more foreground objects are placed correctly relative to the three-dimensional subject model using a predetermined criteria, which could be named a predetermined model criteria. For example, various foreground objects such as coils, hearing protectors or other objects can be identified and then compared to the three-dimensional subject model to see if they are placed correctly on the subject for a given examination target anatomy. This may be beneficial because it may help to ensure that the magnetic resonance imaging protocol is executed properly.

If something is stationary this may mean that within a certain number of frames the subject or the object that is determined as stationary is stationary within these images or moves less than a predetermined amount.

In another embodiment a trained image identifier can be used to automatically identify objects and tag them as foreground objects. Specific geometric models or machine learning can be used to check the placement.

In another embodiment the foreground objects comprise any one of the following: a magnetic resonance imaging coil, a magnetic resonance imaging antenna, an ECG electrode or other physiology sensors, hearing protectors, nurse call, pillows and/or blankets and/or pads, and/or similar objects, and combinations thereof.

In another embodiment execution of the machine-executable instructions further causes the processor to choose a specific absorption rate (SAR) model using the three-dimensional subject model. Execution of the machine-executable instructions further cause the processor to modify the pulse sequence commands at least partially using the specific absorption rate model. This may also include contrast affecting sequence parameters such as the subject height and also weight may be relevant for contrast enhanced magnetic resonance imaging protocols.

In another embodiment execution of the machine-executable instructions further causes the processor to choose a peripheral nerve stimulation model using the three-dimensional subject model. Execution of the machine-executable instructions further cause the processor to modify the pulse sequence commands at least partially using the peripheral nerve stimulation model. This may reduce subject discomfort during a magnetic resonance imaging examination.

In another embodiment execution of the machine-executable instructions further causes the processor to choose a sound pressure model using the three-dimensional subject model. Execution of the machine-executable instructions further cause the processor to modify the pulse sequence commands at least partially using a sound pressure model. A knowledge of the volume of the subject may enable the modeling of sound within the bore of a magnetic resonance imaging magnet.

In another embodiment the medical imaging system is a CT system.

In another embodiment execution of the machine-executable instructions further causes the processor to adjust a CT protocol and/or CT system parameters using the three-dimensional subject model. This may be beneficial because it may provide for a more efficient means of identifying the scan region and/or may eliminate the need for a light visor or the CT survey and may thus reduce x-ray dose.

In another embodiment, execution of the machine executable instructions further causes the processor to automate definition of a start position that defines a Z-coordinate of the subject support corresponding to the start position of a CT scan or localizer;

In another embodiment, execution of the machine executable instructions further causes the processor to automated definition of an end or length that defines a Z-coordinate of the subject support corresponding to the end of a CT scan or localizer In another embodiment, execution of the machine executable instructions further causes the processor to determine a horizontal centering of the subject: i.e. the vertical diameter of the gantry should pass through the head-to-feet center line of the patient.

In another embodiment, execution of the machine executable instructions further causes the processor to determine a vertical centering of the subject: i.e. the horizontal diameter of the gantry should pass through the poster-to-anterior center line of the patient (at least roughly at the target body part)

In another embodiment execution of the machine-executable instructions further causes the processor to choose an X-ray absorption model using the three-dimensional subject model. For example, a knowledge of the thickness of the subject may help in choosing the proper X-ray absorption model and may improve the imaging quality. A knowledge of the three-dimensional subject model may also aid in predicting the location or position of organs at risk (e.g. the thyroid) for which the dose should be kept to a minimum.

In another embodiment execution of the machine-executable instructions further causes the processor to choose a subject support height. This embodiment may be beneficial because it may aid in properly placing the subject within the imaging zone.

In another embodiment the camera system is a three-dimensional camera system. This may be beneficial because it may allow direct measurement of the position of the support surface and/or background objects. The measurement itself may be used for providing a registration of the support surface or even the three-dimensional subject support model. The use of a three-dimensional camera may also be useful for directly measuring the three-dimensional object surface. Likewise, the use of a three-dimensional camera may be useful for directly measuring the visible subject surface. These various measured quantities may then be used to directly calculate the three-dimensional subject model.

In another embodiment execution of the machine-executable instructions further causes the processor to control the camera system to acquire an initial image. Execution of the machine-executable instructions further causes the processor to determine the three-dimensional subject support model at least partially using the initial image.

In another embodiment the camera system is a two-dimensional camera system. In this embodiment the camera system is not a three-dimensional camera. Execution of the machine-executable instructions further causes the processor to assign three-dimensional object models to the one or more background objects in the background object surface image. Execution of the machine-executable instructions further cause the processor to construct the three-dimensional object surface using the assigned three-dimensional object models. The term "assign" as used herein means to fit or infer a model. There may be specific models for specific pillows, blankets, pads, coils and other objects that are within a particular examination room or may be used with the medical imaging system. These may be identified in the series of repeated images and the model can be placed correctly so that it corresponds with the two-dimensional image. In this way the two-dimensional camera can be used to infer or determine the three-dimensional surfaces.

In another embodiment execution of the machine-executable instructions can assign three-dimensional foreground object models to foreground objects in the one of the series of repeated images that contains the subject. This may for example be useful for locating object that are placed on or about the subject such as coils, antennas, or other objects. The visible subject surface may also be determined in this way. In another embodiment execution of the machine-executable instructions further causes the processor to control the camera system to acquire the initial image. Execution of the machine-executable instructions further cause the processor to register the initial image to a three-dimensional subject support model. The three-dimensional subject support model is descriptive of a three-dimensional structure of the support surface.

In another embodiment execution of the machine-executable instructions further causes the processor to approximate gaps in the three-dimensional object surface. For example, if not all portions of the three-dimensional object surface are imaged because during all of the images there was a foreground object and/or a person or subject obscuring it, it may be unknown what the complete three-dimensional object surface is. In this case adjacent measurements on either side of the unknown region can either be extrapolated or interpolated to fill in the missing surface data.

In another embodiment any one of the following is continually updated while the subject support is in the initial position: the detection of the placement of the one or more background objects that at least partially obscure the subject support using repeated images; the detection of the one or more foreground objects that obscure at least a portion of the one or more background objects in the series of repeated images; the construction of the object surface at least partially by stitching together the series of repeated images to replace image regions containing background objects obscured by the one or more foreground objects; the determining of the three-dimensional object surface using the object surface image; the detecting of the subject in the one or more series of repeated images; calculating the subject segmentation of the subject in the one or more series of repeated images; determining the visible subject surface using the subject segmentation and one or more series of repeated images; the calculation of a three-dimensional subject model by estimating a volume defined by the three-dimensional object surface and the subject surface; and combinations thereof. This embodiment may be beneficial because the steps that are performed are constantly updated as the position of the subject or various objects changes.

In another aspect the subject segmentation is calculated after the subject is detected as being stationary in at least a chosen number of sequential images of the series of repeated images.

Stationary may mean that the subject is in the same position for a certain number of frames or the subject moves less than a predetermined amount.

In another embodiment the one or more background objects are chosen from a predetermined list of background objects. This may be beneficial because if the list of background objects is limited then it may improve the ability to identify objects or even to provide a suitable model for a two-dimensional image.

In another embodiment the one or more foreground objects are chosen from a predetermined list of foreground objects. Likewise, this may facilitate the identification of the foreground objects by limiting the possibilities. In the case of both the background and foreground objects this may be reasonable because typically for medical imaging systems the objects which are allowed to be placed into the imaging system are limited.

In another aspect the invention provides for a computer program product comprising machine-executable instructions for execution by a processor controlling the medical imaging system for acquiring medical imaging data from a subject within an imaging zone. The medical imaging system further comprises a subject support with a support surface. The support surface is configured for receiving the subject. The subject support is configured for supporting the subject in an initial position. In the initial position the subject is outside of the imaging zone. In the second position the subject support is configured for supporting at least a portion of the subject within the imaging zone. The medical imaging system further comprises a camera system configured for imaging the support surface when the subject support is in the initial position. Execution of the machine-executable instructions further causes the processor to place the subject support in the initial position. Execution of the machine-executable instructions further cause the processor to control the camera system to repeatedly acquire a series of repeated images.

Execution of the machine-executable instructions further causes the processor to detect the placement of one or more background objects that at least partially obscure the support surface using the series of repeated images. Execution of the machine-executable instructions further cause the processor to detect one or more foreground objects that obscure at least a portion of the one or more background objects in the series of repeated images.

Execution of the machine-executable instructions further cause the processor to construct a background object surface image at least partially by stitching together the series of repeated images to replace image regions containing background objects obscured by the one or more foreground objects. Execution of the machine-executable instructions further cause the processor to determine a three-dimensional object surface using the background object surface image. Execution of the machine-executable instructions further cause the processor to detect the subject in the one of the series of repeated images. Execution of the machine-executable instructions further cause the processor to calculate a subject segmentation of the subject in the one of the series of repeated images.

Execution of the machine-executable instructions further cause the processor to determine a visible subject surface using the subject segmentation and the one of the series of repeated images. Execution of the machine-executable instructions further cause the processor to calculate a three-dimensional subject model by estimating a volume defined by the three-dimensional object surface and the visible subject surface. The benefits of this embodiment have been previously discussed.

In another aspect the invention provides for a method of operating a medical instrument. The medical instrument comprises a medical imaging system for acquiring medical imaging data from a subject within an imaging zone. The medical instrument further comprises a subject support with a support surface. The support surface is configured for receiving the subject. The subject support is configured for supporting the subject in an initial position. In the initial position the subject is outside of the imaging zone. In a second position the subject support is configured for supporting at least a portion of the subject within the imaging zone. The medical instrument further comprises a camera system configured for imaging the support surface when the subject support is in the initial position.

The method comprises placing the subject support in the initial position. The method further comprises controlling the camera system to repeatedly acquire a series of repeated images. The method further comprises detecting the placement of one or more background objects that at least partially obscure the support surface using the series of repeated images. The method further comprises detecting one or more foreground objects that obscure at least a portion of the one or more background objects and/or the subject support in the series of repeated images.

The method further comprises constructing a background object surface image at least partially by stitching together the series of repeated images to replace image regions containing background objects obscured by the one or more foreground objects. The method further comprises determining a three-dimensional object surface using the background object surface image. The method further comprises detecting a subject in one of the series of repeated images. The method further comprises calculating a subject segmentation of the subject in the one of the series of repeated images. The method further comprises determining a visible subject surface using the subject segmentation and the one of the series of repeated images. The method further comprises calculating a three-dimensional subject model by estimating a volume defined by the three-dimensional object surface and the visible subject surface.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three-dimensional data that has been acquired using a medical imaging system or scanner. A medical imaging system is defined herein as a apparatus adapted for acquiring information about the physical structure of a patient and construct sets of two dimensional or three dimensional medical imaging data. Medical imaging data can be used to construct visualizations which are useful for diagnosis by a physician. This visualization can be performed using a computer.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical imaging data. A Magnetic Resonance Imaging (MRI) image or MR image is defined herein as being the reconstructed two or three dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
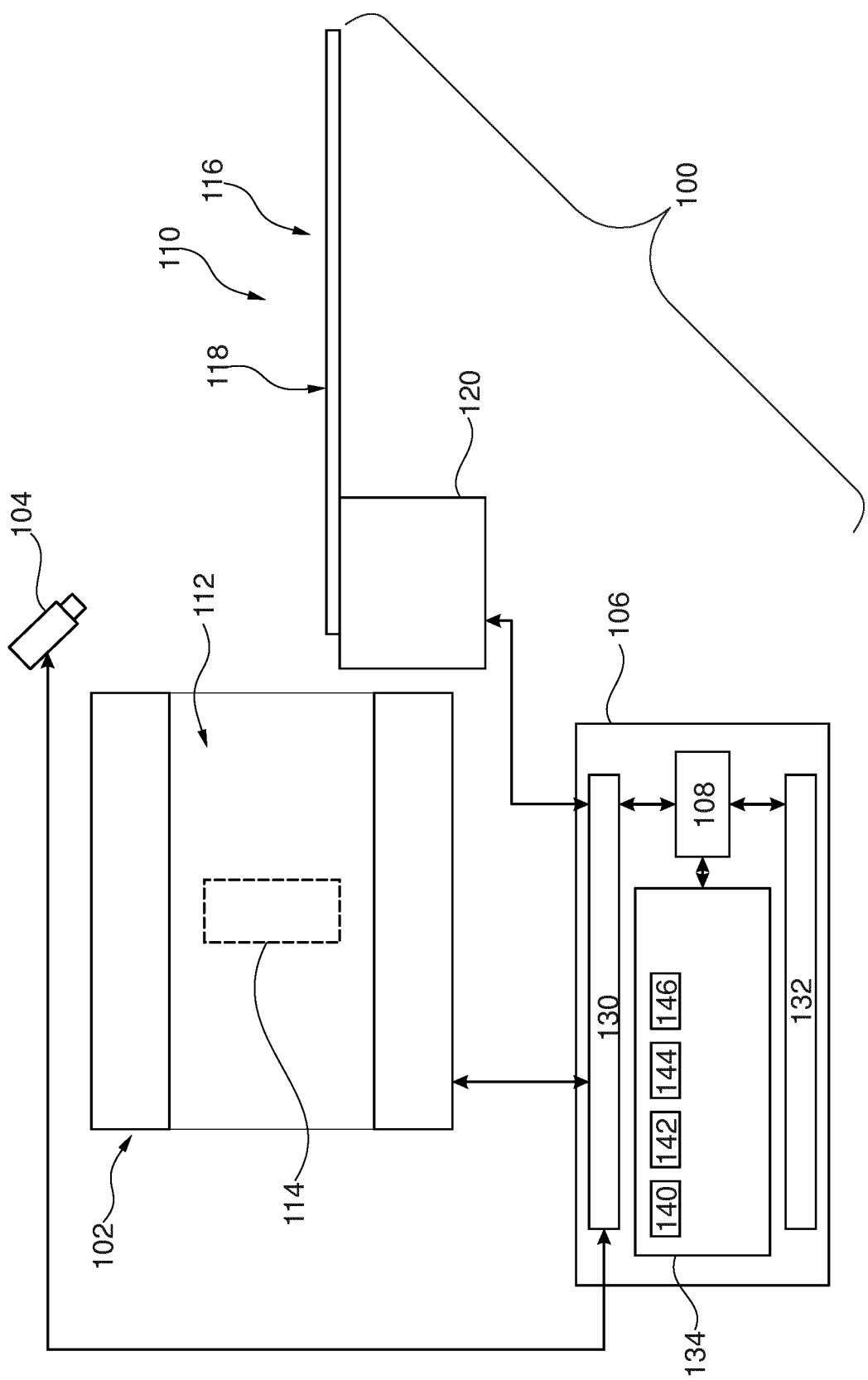
FIG. 1 illustrates an example of a medical instrument.

FIG. 1 illustrates an example of a medical instrument 100. The medical instrument 100 comprises a medical imaging system 102. The medical instrument 100 also comprises a camera system 104. 104 is intended to represent both three-dimensional and two-dimensional cameras.

The medical instrument 100 is further shown as comprising a computer system which provides a processor 108. The processor 108 is configured for controlling the medical instrument 100. The medical instrument is further shown as comprising a subject support 110.

The medical imaging system 102 is intended to be representative. In this example is it a cylindrical type with a bore 112 for receiving a subject. There is an imaging zone 114 where medical imaging data can be acquired from a subject. The medical imaging system 102 may for example be used to represent both CT and MRI systems.

The subject support 110 is shown in an initial position 116. The subject support 110 has a support surface 118 configured for receiving a subject. Also shown is a support actuator 120 that can move the support surface 118 into the bore 112 of the medical imaging system 102. In the initial position 116 the camera system 104 is able to image the support surface 118.

The computer system 106 is shown as comprising a hardware interface 130 that enables the processor 108 to communicate with and control the other components of the medical instrument 100. The hardware interface is shown as being connected to the camera system 104, the medical imaging system 102, and the support actuator 120. The support actuator 120 may for example be used for moving the position of the support surface 118 both into the bore and also in a vertical direction for controlling the height position of the subject in something embodiments.

The computer system 106 is further shown as containing a user interface 132 and computer memory 134. The memory 134 may be any combination of memory which is accessible to the processor 108. This may include such things as main memory, cached memory, and also non-volatile memory such as flash RAM, hard drives, or other storage devices. In some examples the memory 134 may be considered to be a non-transitory computer-readable medium.

The computer memory 134 is shown as containing machine-executable instructions 140 that enable the processor 108 to control the medical instrument 100 and perform various tasks such as performing computations, doing image processing and reconstructing various images. The computer memory 134 is further shown as containing a series of repeated images 142. In the example in FIG. 1 there are no objects or subjects on the support surface 118. The images so far are just simply of the support surface itself. The memory 134 is further shown as containing a three-dimensional subject support model 144 that models the three-dimensional surface of the support surface 118. The determinization of the three-dimensional subject support model 144 is optional. In some examples portions of the support surface are located in images containing other background objects.

The memory is further shown as containing a registration of the subject support model 144 to the series of repeated images 146. This registration is optional. For example, if the camera system 104 is a two-dimensional camera the subject support model 144 may be an a priori model which is then registered to the series of repeated images 142. If the camera system 104 is a three-dimensional camera system the registration 146 and the subject support model 144 may be measured itself by the camera system 104.

Figure 2:
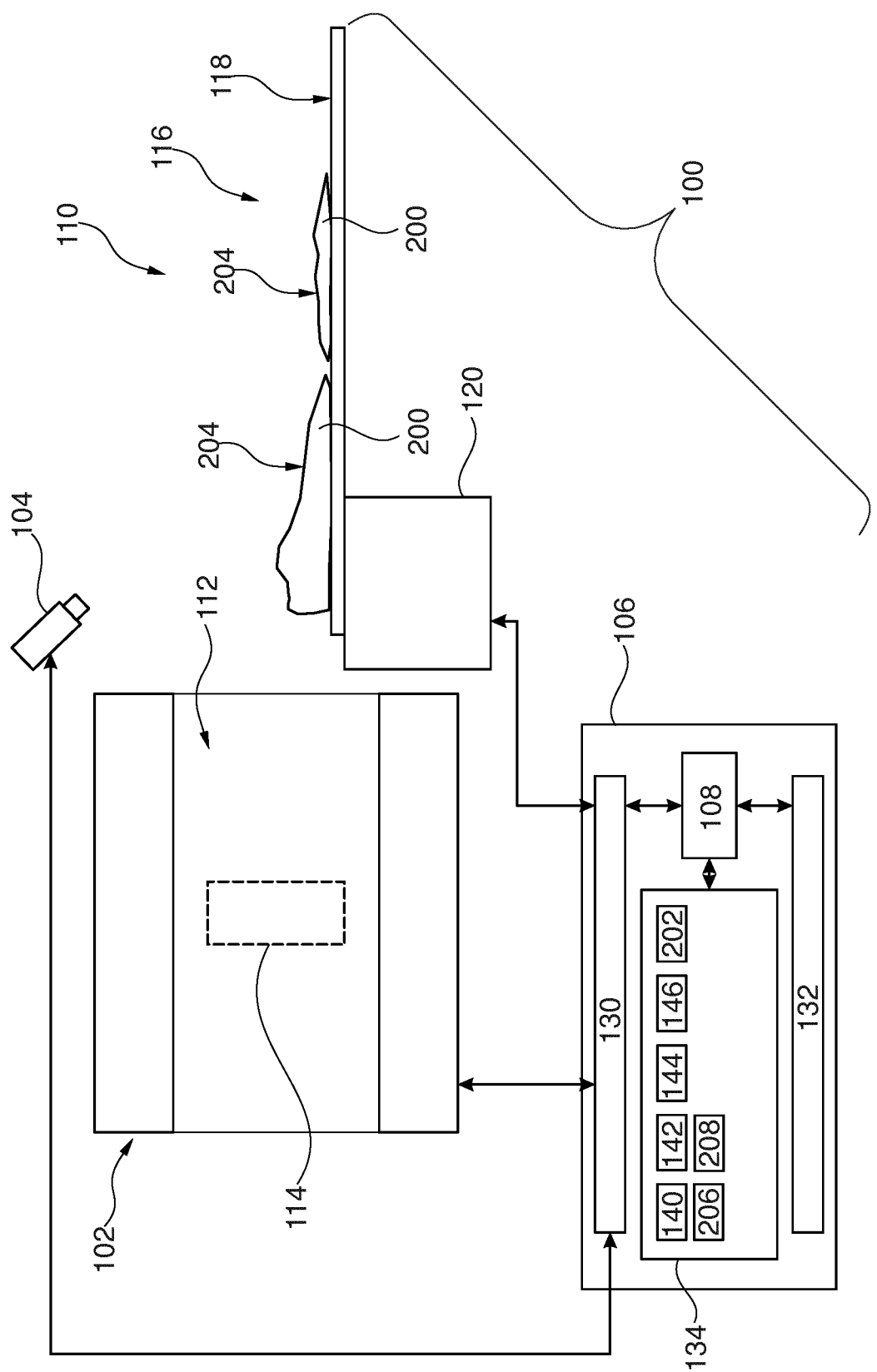
FIG. 2 shows an additional view of the medical instrument of FIG. 1.

FIG. 2 shows a further view of the medical instrument 100. Again, the subject support 110 is in the initial position 118. Several background objects 200 are shown as having been placed onto the support surface 118. The camera system 104 has acquired a background object surface image 202. The background object surface image 202 shows the support surface 118 which is partially obscured by the surface 204 of the background objects 200. The image of the surface of the background object 204 may be used to determine a three-dimensional object surface 208, which is stored in the memory 134. If an operator is placing the background objects 200 onto the support surface 118 the camera system 104 will not be able to image the background objects 200 if they are obscured. The series of repeated images 142 can be used to stitch together the complete background object surface image 202 which is then used to construct the three-dimensional object surface 208. In the case that some portions of the surface of the background object 204 remain obscured portions of the three-dimensional object surface 208 can be interpolated or extrapolated.

Figure 3:
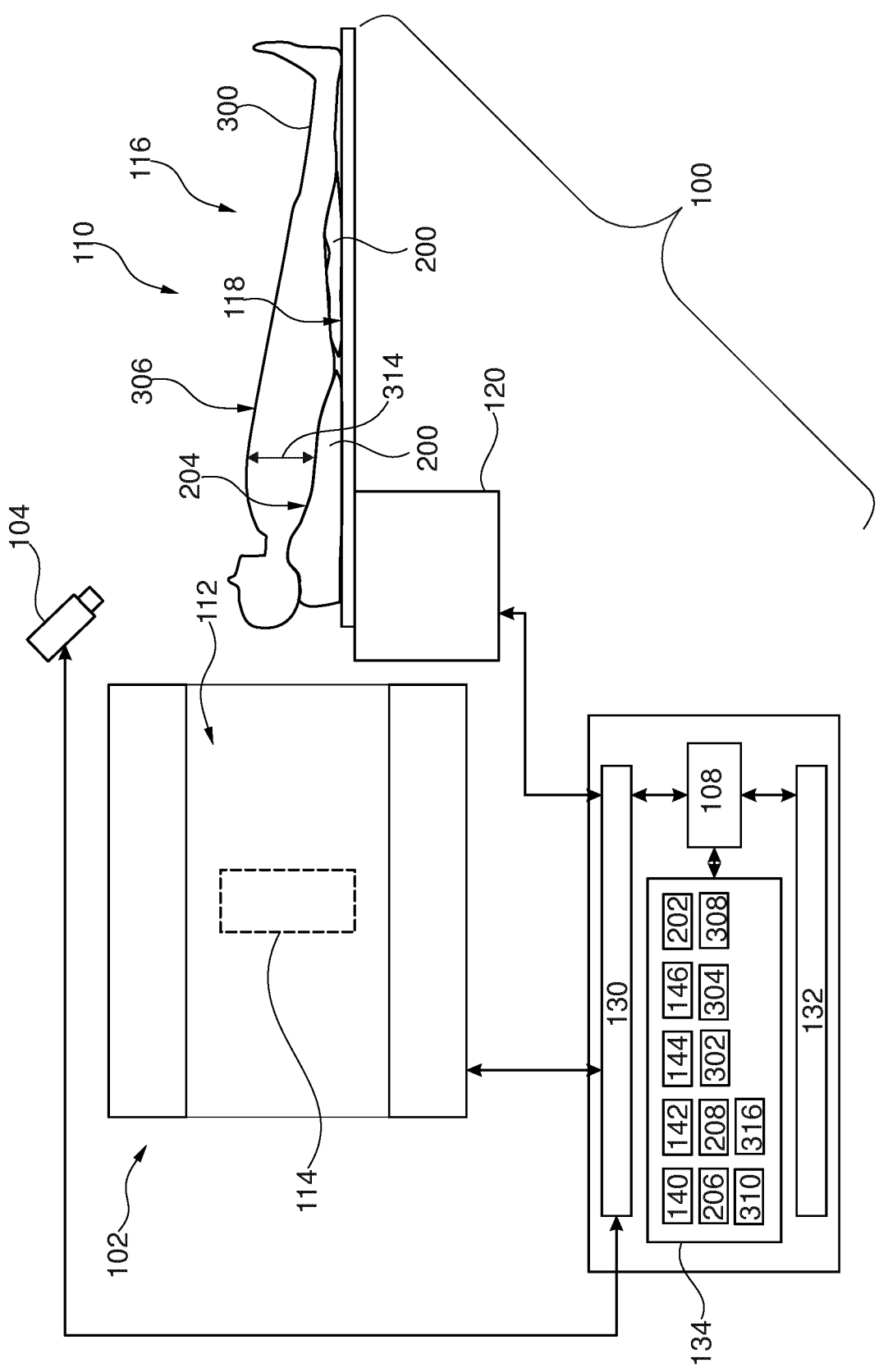
FIG. 3 shows an additional view of the medical instrument of FIG. 1.

FIG. 3 shows a further view of the medical instrument 100. In this example, a subject 300 is seen as reposing on the subject support and the background objects 200. The camera system 104 is able to image the subject 300 and the subject 300 has been identified in one of the series of repeated images 302. The processor 108 then segmented the one of the series of repeated images 302 to determine a subject segmentation 304. This subject segmentation 304 was used to determine a visible subject surface 308 in the one of the series of repeated images 302. This corresponds to the physical surface of the subject 306. The position of the camera 104 is illustrative, the camera can be placed in any location where it can image the subject surface 308.

Using the visible subject surface 308 a three-dimensional subject model 310 is developed. In the case of a three-dimensional camera the three-dimensional subject model 310 can be measured directly. In the case of a two-dimensional camera system a model may be fit to the visible subject surface 308. The three-dimensional subject model 310 defines a volume 314 defined by the physical surface of the subject 306 and the surface of the background objects 204. The surface of the background objects may include the support surface 118. The three-dimensional subject support model 310 can for example be used to calculate a second position 316 to move the subject support 110 too.

Figure 4:
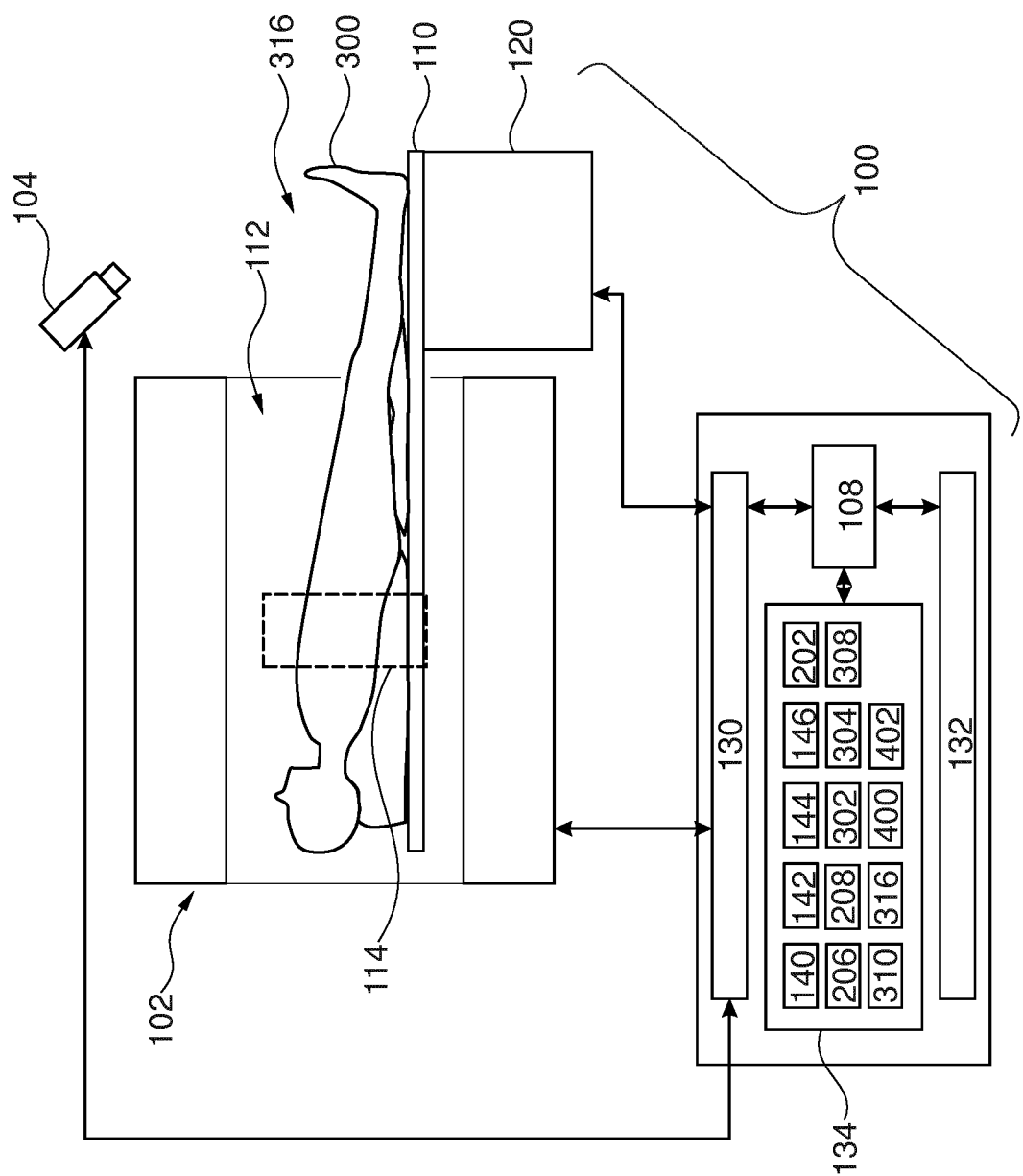
FIG. 4 shows an additional view of the medical instrument of FIG. 1.

FIG. 4 shows a further view of the medical instrument 100. In FIG. 4 the processor has controlled the support actuator 120 to move the subject support 110 into the second position 316. A portion of the subject 300 is now within the imaging zone 114. The processor 108 then controlled the medical imaging system 102 to acquire the medical image data 400. The memory 134 is further shown as containing a medical image 402 that has been reconstructed from the medical image data 400.

Figure 5:
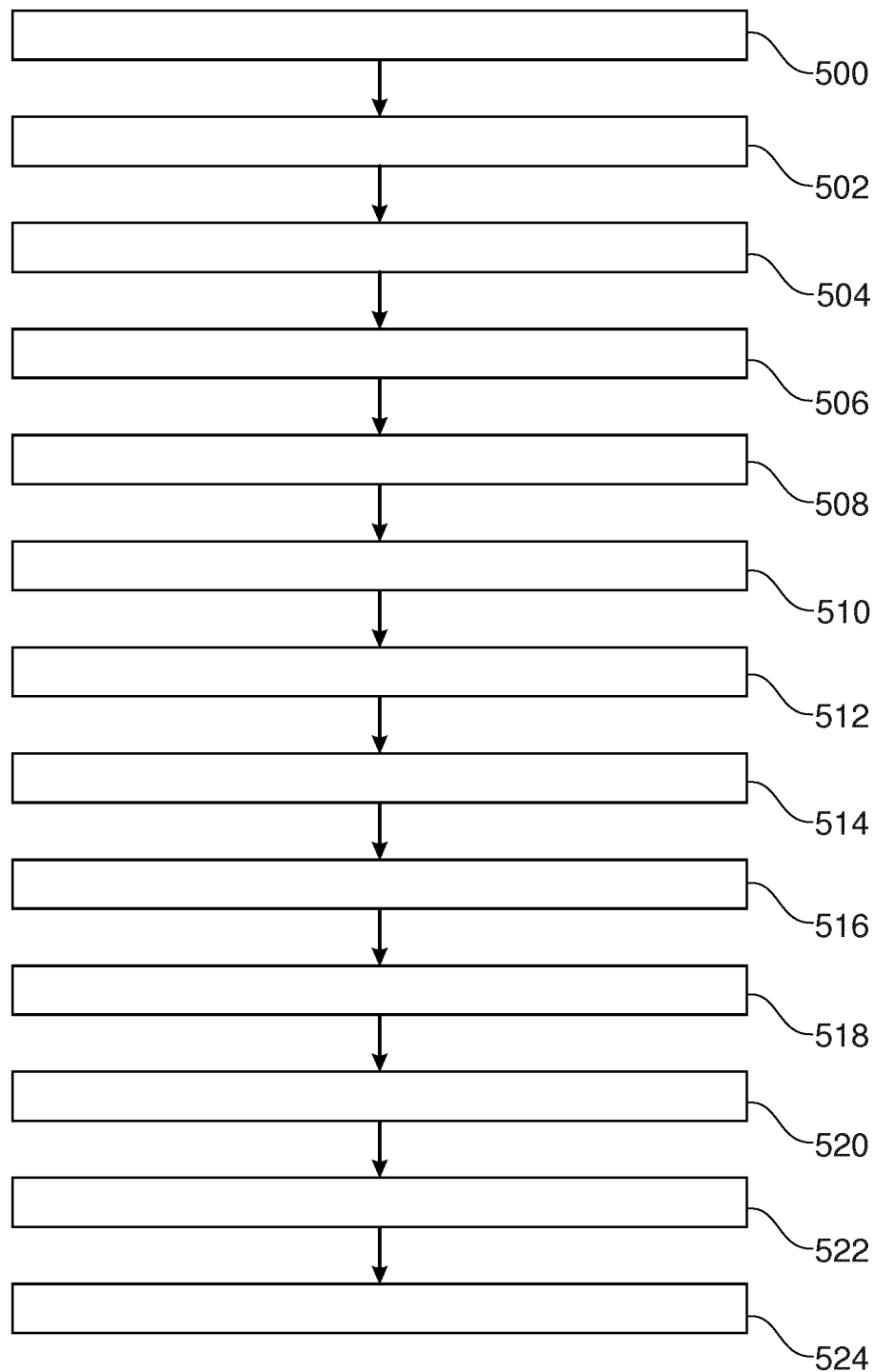
FIG. 5 shows a flow chart which illustrates a method of using the medical instrument of FIG. 1.

FIG. 5 shows a flowchart which illustrates a method of operating the medical instrument 100 illustrated in FIGS. 1-4. First in step 500 the subject support 110 is placed into the initial position 116. Next in step 502, the camera system 104 is controlled to repeatedly acquire a series of repeated images 142. Next in optional step 504 a registration 146 of the subject support model 144 to the series of repeated images 142 is received. Next in step 506 the placement of one or more background objects 200 is detected that at least partially obscure the subject support surface 118 within the series of repeated images 142. The optional registration 146 could also be performed when there are background objects 200 on the subject support. Then in step 508 one or more foreground objects are detected that obscure at least a portion of the one or more background objects 200 in the series of repeated images 142.

Then in step 510 the background object surface image 202 is constructed by stitching together the series of repeated images to replace image regions containing background objects obscured by the one or more foreground objects. Then in step 512 the three-dimensional object surface is determined using the background object surface image 202. Next in step 514 the subject 300 is detected in one 302 of the series of repeated images 142. Next in step 516 the subject segmentation 304 is calculated using the one 302 of the series of repeated images 142. Next in step 518 the visible subject surface 308 is determined using the subject segmentation 304 and the one of the series of repeated images 302. Then in step 520 the three-dimensional subject model 310 is determined by estimating a volume 314 defined by the three-dimensional subject support model 144, the three-dimensional object surface 208.

In step 522 the subject support 110 is moved from the initial position 116 to the second position 316. The second position 316 is determined at least partially using the three-dimensional subject model 310. Finally, in step 524, the medical imaging data 400 is acquired from the subject 300. The method may also proceed by reconstructing the medical image 402 from the medical image data 400 in some examples.

Figure 6:
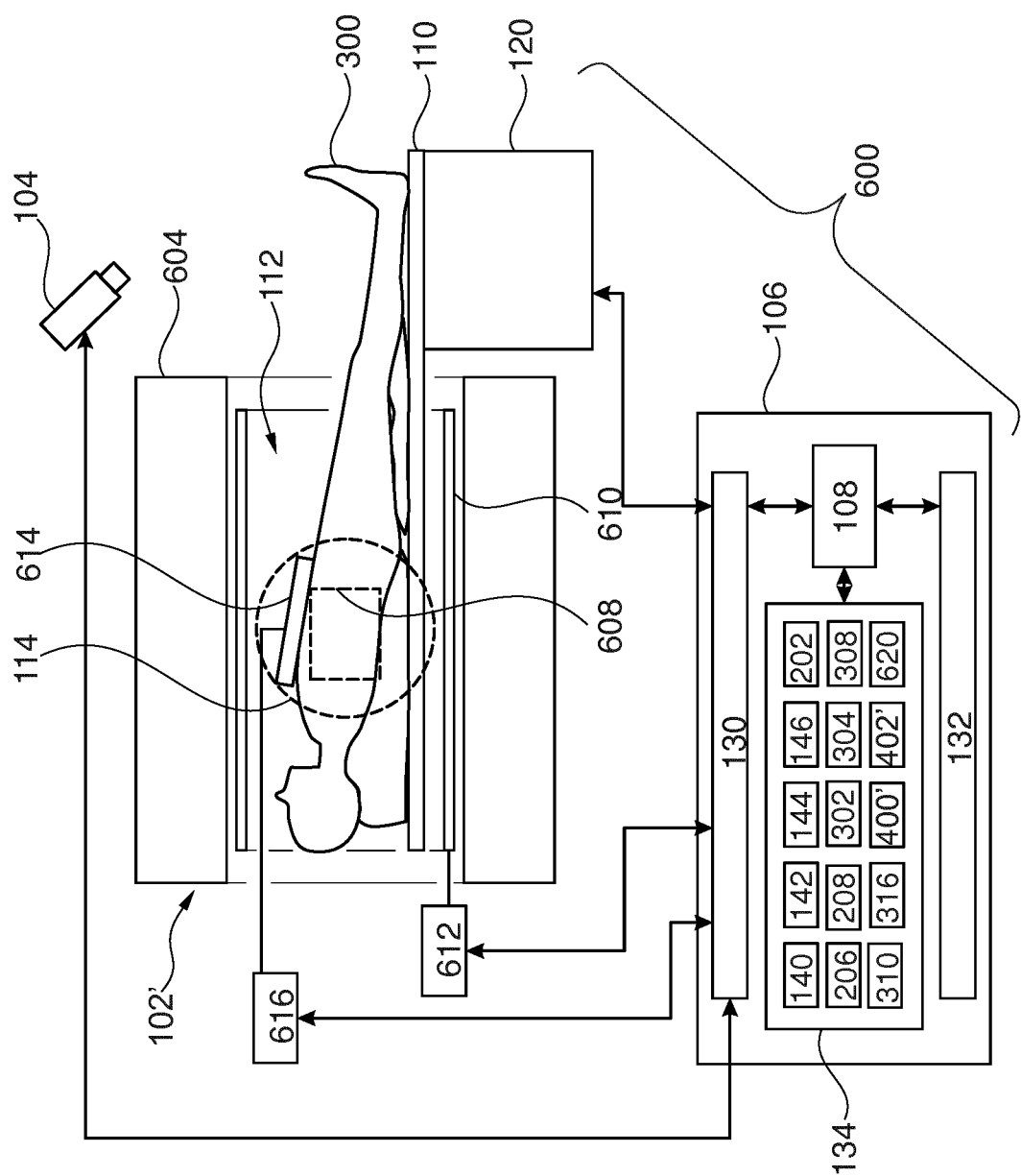
FIG. 6 illustrates a further example of a medical instrument.

FIG. 6 illustrates a further example of a medical instrument 600. The medical instrument 600 in FIG. 6 is similar to the medical instrument 100 illustrated in FIGS. 1-4 except that in this particular case the medical imaging system is a magnetic resonance imaging system 102'.

The magnetic resonance imaging system 102' comprises a magnet 104. The magnet 104 is a superconducting cylindrical type magnet with a bore 112 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 112 of the cylindrical magnet 604 there is an imaging zone 114 where the magnetic field is strong and uniform enough to perform magnetic resonance imaging. A region of interest 608 is shown within the imaging zone 114. The magnetic resonance data that is acquired typically acquired for the region of interest. A subject 300 is shown as being supported by a subject support 110 such that at least a portion of the subject 300 is within the imaging zone 114 and the region of interest 608.

Within the bore 112 of the magnet there is also a set of magnetic field gradient coils 610 which is used for acquisition of preliminary magnetic resonance data to spatially encode magnetic spins within the imaging zone 114 of the magnet 604. The magnetic field gradient coils 610 connected to a magnetic field gradient coil power supply 612. The magnetic field gradient coils 610 are intended to be representative. Typically magnetic field gradient coils 610 contain three separate sets of coils for spatially encoding in three orthogonal spatial directions. A magnetic field gradient power supply supplies current to the magnetic field gradient coils. The current supplied to the magnetic field gradient coils 610 is controlled as a function of time and may be ramped or pulsed.

Adjacent to the imaging zone 608 is a radio-frequency coil 614 for manipulating the orientations of magnetic spins within the imaging zone 608 and for receiving radio transmissions from spins also within the imaging zone 608. The radio frequency antenna may contain multiple coil elements. The radio frequency antenna may also be referred to as a channel or antenna. The radio-frequency coil 614 is connected to a radio frequency transceiver 616. The radio-frequency coil 614 and radio frequency transceiver 616 may be replaced by separate transmit and receive coils and a separate transmitter and receiver. It is understood that the radio-frequency coil 614 and the radio frequency transceiver 616 are representative. The radio-frequency coil 614 is intended to also represent a dedicated transmit antenna and a dedicated receive antenna. Likewise the transceiver 616 may also represent a separate transmitter and receivers. The radio-frequency coil 614 may also have multiple receive/transmit elements and the radio frequency transceiver 616 may have multiple receive/transmit channels. For example if a parallel imaging technique such as SENSE is performed, the radio-frequency could 614 will have multiple coil elements. The transceiver 616 and the gradient controller 612 are also shown as being connected to the hardware interface 130 of the computer system 106.

The medical imaging data in this example is magnetic resonance imaging data 400' and the magnetic resonance imaging data 400' has been reconstructed into a magnetic resonance image 402'. The memory 134 is further shown as containing pulse sequence commands 620 that enable the processor 108 to control the magnetic resonance imaging system 102' to acquire the magnetic resonance imaging data 400'. The pulse sequence commands 620 are configured for controlling the magnetic resonance imaging system 102' to acquire a series of magnetic resonance data from the subject 300 according to a quantitative magnetic resonance imaging protocol Improvements of examination workflows in the radiology are of high business interest due to the potential associated healthcare cost reduction. Camera sensors (camera systems) including depth sensors (three dimensional cameras) are ideal sensor candidates to provide information about the patient, moveable medical equipment and accessories, and further imaging modality devices. To extract accurately the relevant information about patient and devices, these may be segmented out from the remaining background environment. However, while the scanner room is a typically controlled environment, the determination of background elements such as patient support, pillows, blankets, and coils placed under the patient is challenging for at least two reasons:

Clinical workflows are very dynamic and variable between staff members and hospitals, so that non-standard/non-expected devices may be present on the patient support and background object may all undergo changes until the patient is in final and comfortable resting position for scanning Background objects may be partly and temporally obstructed by the operator and/or the patient.

This makes standard techniques based on overall motion analysis over the whole scene or object recognition inapplicable.

Examples may possibly provide the following solution:

Since the background is static over much longer time periods than the examination subjects, staff and accessories, examples may apply spatio-temporal stitching techniques to assemble an up-to-date background image (background surface image) and to further update it dynamically until the patient is in the final and comfortable resting position for scanning.

The system (medical instrument), possibly consisting of a depth camera (camera system), acquires images continuously and detects image patches that are static over time. These image patches are then stitched together to one overall reference background image. See the example in FIG. 7 below. Preparing the table support for the examination will often obstruct relevant background scenery partly but only temporarily.

The starting point is an image where no patient is present. At each time where motion is detected within a patch (e.g. due to the tech moving or some pillows being shifted around), the image patch is updated with the content corresponding to the time point where the scene in the image patch becomes static again. This is done until the system detects the presence of the patient (subject) on the table. Patient detection can be done by several means (image processing technique, data from another sensor, or manually). At this time point, an accurate background computation is available and the exact patient outline can be segmented. Patches that have never become visible between the last patient until the current patient comes to rest on the patient support will be filled by inter/extrapolation.

In some examples, the background image can still be updated to account for displacement of object placed under the patient. (e.g. pillows may be added below him, e.g.

below his legs for a more comfortable position or he may adapt the head pillow to his needs). The system may also detect the patient and his body parts, for example using tracking methods and the initial patient segmentation and use visible patches that do not belong to the patient as much as possible to estimate changes in the background scenery. Typically, there is a limited number of devices so object recognition techniques could be applied and objects detected before which have not left the scene could be fitted to the most current data.

Using this technique, the system can specify a confidence level of the measured parameters which could be e.g. patient weight, height, position and orientation and it could apply the background corrections for the best possible estimate.

Figure 7:
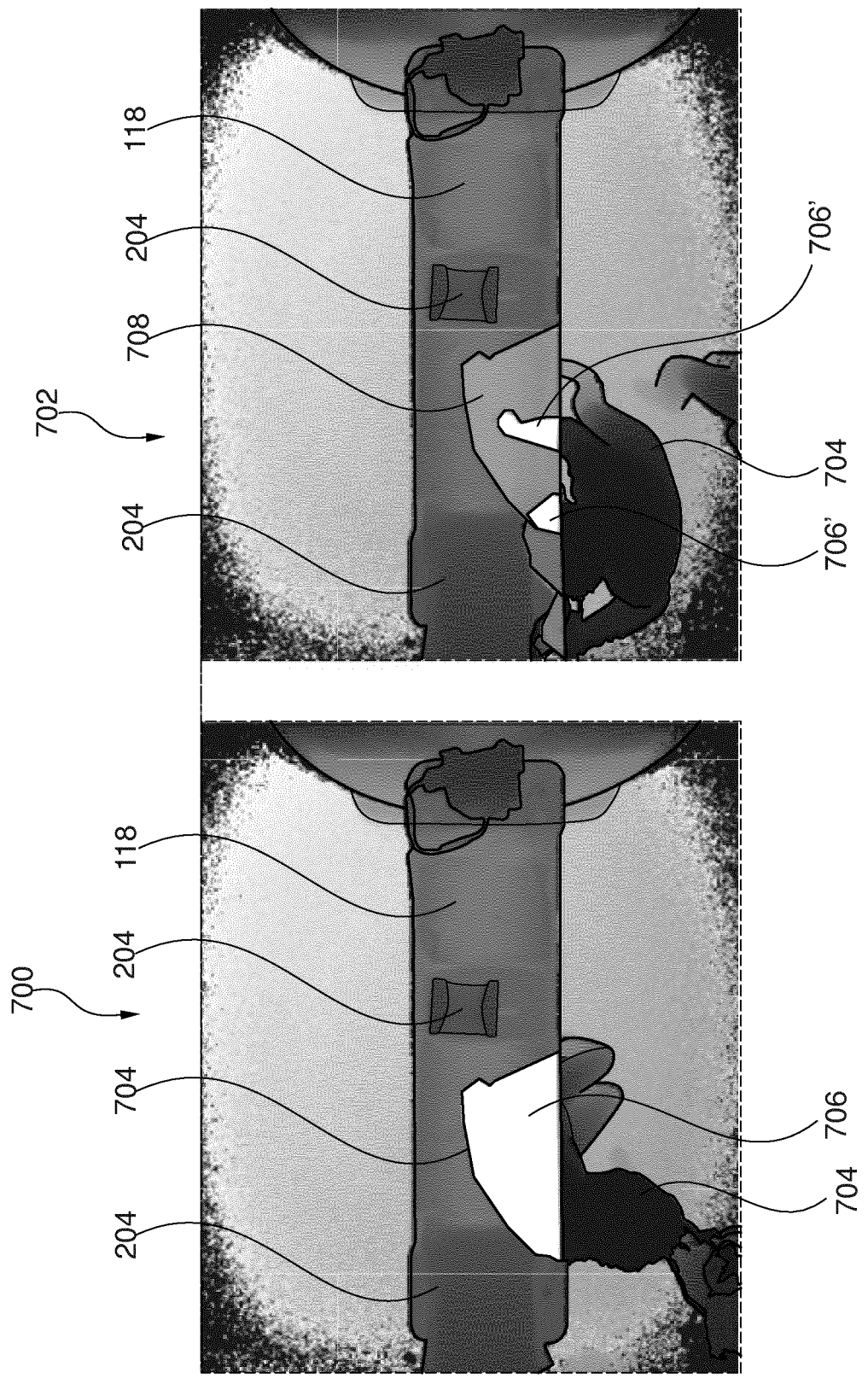
FIG. 7 show several images of a subject support.

FIG. 7 shows a first image 700 and a second image 702. The two consecutive frames (images) 700, 702 show decreasing residual patches over time for the patient support background estimation. The two images 700, 702 show segmentations. In the first image 700 the support surface 118 is visible along with several surfaces of background objects 204. A foreground object 704 which is a person is shown as obscuring a region 706. Portions of the support surface 118 and the surface of the background object 204 were not able to be imaged in the region labeled 706.

The second image 702 shows the same view of the support surface 118 and the surface of the background objects 204. However, in this case the foreground object 704 which is again a person, has moved to a different position. There are two regions labeled 706' which are regions which are obscured both in the first image 700 and the second image 702. In the region 706' there is no image of the support surface 118 or of the surface of the background object 204. However, the region 708 has been stitched from the first image 700. It can be seen that if a larger number of images are acquired further regions can be stitched and the regions 706' can be filled also. In some examples, if the region 706' cannot be filled, then the data in these regions can be interpolated or extrapolated.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 medical imaging system
102' magnetic resonance imaging system
104 camera system
106 computer system
108 processor
110 subject support
112 bore
114 imaging zone
116 initial position
118 support surface
120 support actuator
130 hardware interface
132 user interface
134 memory
140 machine executable instructions
142 series of repeated images
144 three-dimensional subject support model
146 registration of the three-dimensional subject support model to series of repeated images
200 background object
202 background object surface image
204 surface of background object
208 three-dimensional object surface
300 subject
302 one of series of repeated images which shows subject
304 subject segmentation
306 surface of subject
308 visible subject surface
310 three-dimensional subject model
314 volume defined between surface of subject and surface of background object
316 second position
400 medical image data
400 magnetic resonance imaging data
402 medical image
402 magnetic resonance image
500 place the subject support in the initial position
502 control the camera system to repeatably acquire a series of repeated images
504 receive a registration of a three-dimensional subject support model to the series of repeated images
506 detect the placement of one or more background objects that at least partially obscure the support surface within the series of repeated images
508 detect one or more foreground objects that obscure at least a portion of the one or more background objects in the series of repeated images
510 construct a background object surface image at least partially by stitching together the series of repeated images to replace image regions containing background objects obscured by the one or more foreground objects
512 determine a three-dimensional object surface using the background object surface image
514 detect the subject in one of the series of repeated images
516 calculate a subject segmentation of the subject in the one of the series of repeated images
518 determine a visible subject surface using the subject segmentation and the one of the series of repeated images
520 calculate a three-dimensional subject model by estimating a volume defined by the three-dimensional subject support model
522 move the subject support from the initial position to the second position
524 acquire the medical imaging data
604 magnet
612 bore of magnet
608 region of interest
610 magnetic field gradient coils 612 magnetic field gradient coil power supply
614 radio-frequency coil
616 transceiver
620 pulse sequence commands
600 medical instrument
700 first image
702 second image
704 foreground object
706 obscured region
706' obscured region
708 stitched region

The invention claimed is:

1. A medical instrument comprising:
a medical imaging system for acquiring medical imaging data from a subject within an imaging zone;
a subject support with a support surface, wherein the support surface is configured for receiving the subject, wherein the subject support is configured for supporting the subject in an initial position wherein in the initial position the subject is outside of the imaging zone;
a camera system configured for imaging the support surface when the subject support is in the initial position;
a memory comprising machine executable instructions; and
a processor for controlling the medical instrument, wherein execution of the machine executable instructions causes the processor to:
place the subject support in the initial position;
control the camera system to repeatably acquire successive images;
detect the placement of one or more background objects that at least partially obscure the support surface within the successive images;
detect one or more foreground objects that obscure at least a portion of the one or more background objects in the successive images;
construct a background object surface image at least partially by stitching together the successive images to replace image regions containing background objects obscured by the one or more foreground objects;
determine a three-dimensional object surface using the background object surface image;
detect the subject in one of the successive images from the one or more foreground objects;
calculate a subject segmentation of the subject in in at least one of the successive images;
determine a visible subject surface using the subject segmentation and the one of the successive images; and
calculate a three-dimensional subject model by estimating a volume defined by the three-dimensional object surface and the visible subject surface.

2. The medical instrument of claim 1, wherein the subject support is configured for transporting the subject from an initial position to a second position, wherein in the second position the subject support is configured for supporting at least a portion of the subject within the imaging zone wherein execution of the machine executable instructions further causes the processor to move the subject support from the initial position to the second position, wherein the second position is determined at least partially using the three-dimensional subject model.

3. The medical instrument of claim 1, wherein the medical imaging system is a magnetic resonance imaging system, wherein the memory further contains pulse sequence commands configured for controlling the magnetic resonance imaging system to acquire the medical imaging data from a region of interest in the imaging zone.

4. The medical instrument of claim 3, wherein execution of the machine executable instructions further causes the processor to:
fit the region of interest to the three-dimensional subject model; and
modify the pulse sequence commands to image the fitted region of interest.

5. The medical instrument of claim 3, wherein execution of the machine executable instructions further causes the processor to:
identify at least a portion of the one or more foreground objects that are stationary in at least a predetermined number of sequential images in the successive images;
determine if the at least a portion of the one or more foreground objects are placed correctly relative to the three-dimensional subject model using a predetermined criteria.

6. The medical instrument of claim 3, wherein execution of the machine executable instructions further causes the processor to:
choose at least one of a Specific Absorption Model, a peripheral nerve stimulation model, a sound pressure model, a subject height, and/or a subject weight using the three-dimensional subject model; and
modify the pulse sequence commands at least partially based on the chosen Specific Absorption Model, a peripheral nerve stimulation model, a sound pressure model, the subject height, and/or the subject weight.

7. The medical instrument of claim 1, wherein the medical imaging system is a CT system, wherein execution of the machine executable instructions further causes the processor to perform one or more of the following:
automate definition of a start of a localizer;
automated definition of an end or length of the localizer;
determine a horizontal centering of the subject;
determine a vertical centering of the subject;
choose an x-ray absorption model using the three-dimensional subject model; or
choose a subject support height.

8. The medical instrument of claim 1, wherein the camera system is a three-dimensional camera system.

9. The medical instrument of claim 1, wherein the camera system is a two-dimensional camera system, wherein execution of the machine executable instructions further causes the processor to:
assign three-dimensional object models to the one or more background objects in the background object surface image;
construct the three-dimensional object surface using the assigned three-dimensional object models.

10. The medical instrument of claim 1, wherein execution of the machine executable instructions further causes the processor to approximate gaps in the three-dimensional object surface.

11. The medical instrument of claim 1, wherein at least one of the following is continually updated while the subject support is in the initial position:
detection of the placement of one or more background objects that at least partially obscure the support surface within the successive images;
detection of the one or more foreground objects that obscure at least a portion of the one or more background objects in the successive images;

construction of the object surface image at least partially by stitching together the successive images to replace image regions containing background objects obscured by the one or more foreground objects;

determining the three-dimensional object surface using the object surface image;

detecting the subject in one of the successive images from the one or more foreground objects;

calculating the subject segmentation of the subject in the one of the successive images;

determining the visible subject surface using the subject segmentation and the one of the successive images; or calculation a three-dimensional subject model by estimating a volume defined by the three-dimensional object surface and the visible subject surface.

12. The medical instrument of claim 1, wherein the subject segmentation is calculated after the subject is detected as being stationary in at least a chosen number of successive images.

13. The medical instrument of claim 1, wherein at least one of
the one or more background objects are chosen from a predetermined list of background objects; or the one or more foreground objects are chosen from a predetermined list of foreground objects.

14. A computer program product comprising:
machine executable instructions stored on a non-transitory computer readable medium for execution by a processor controlling a medical instrument, wherein the medical instrument includes a medical imaging system for acquiring medical imaging data from a subject within an imaging zone, wherein the medical imaging system further comprises a subject support with a support surface, wherein the support surface is configured to receive the subject, wherein the subject support is configured to support the subject in an initial position, wherein in the initial position the subject is outside of the imaging zone, wherein the medical imaging system further comprises a camera system configured to image the support surface when the subject support is in the initial position;

wherein execution of the machine executable instructions causes the processor to:
place the subject support in the initial position;
control the camera system to repeatably acquire successive images;
detect the placement of one or more background objects that at least partially obscure the support surface using the successive images;
detect one or more foreground objects that obscure at least a portion of the one or more background objects in the successive images;
construct a background object surface image at least partially by stitching together the successive images to replace image regions containing background objects obscured by the one or more foreground objects;
determine a three-dimensional object surface using the background object surface image;
detect the subject from the one or more foreground objects in one of the successive images;
calculate a subject segmentation of the subject in the one of the successive images;
determine a visible subject surface using the subject segmentation and the one of the successive images; and
calculate a three-dimensional subject model by estimating a volume defined by the three-dimensional object surface and the visible subject surface.

15. A method of operating a medical instrument, wherein the medical instrument comprises a medical imaging system for acquiring medical imaging data from a subject within an imaging zone, wherein the medical instrument further includes a subject support with a support surface, wherein the support surface is configured to receive the subject, wherein the subject support is configured to support the subject in an initial position, wherein in the initial position the subject is outside of the imaging zone, wherein the medical instrument further comprises a camera system configured to image the support surface when the subject support is in the initial position,
wherein the method comprises:
placing the subject support in the initial position;
controlling the camera system to repeatably acquire successive images;
detecting the placement of one or more background objects that at least partially obscure the support surface using the successive images;
detecting one or more foreground objects that obscure at least a portion of the one or more background objects in the successive images;
constructing a background object surface image at least partially by stitching together the successive images to replace image regions containing background objects obscured by the one or more foreground objects;
determining a three-dimensional object surface using the background object surface image;
detecting the subject from the one or more foreground objects in one of the successive images;
calculating a subject segmentation of the subject in the one of the successive images;
determining a visible subject surface using the subject segmentation and the one of the successive images; and
calculating a three-dimensional subject model by estimating a volume defined by the three-dimensional object surface and the visible subject surface.

* * * * *